United States Patent [19]

Erpenbach et al.

[11] Patent Number: 4,556,644
[45] Date of Patent: Dec. 3, 1985

[54] PROCESS FOR PURIFYING AND RECOVERING CONTAMINATED CATALYST SOLUTION OBTAINED IN THE CARBONYLATION OF METHYL ACETATE AND/OR DIMETHYLETHER

[75] Inventors: Heinz Erpenbach, Cologne; Klaus Gehrmann; Winfried Lork, both of Erftstadt; Peter Prinz, Hürth, all of Fed. Rep. of Germany

[73] Assignee: Hoechst Aktiengesellschaft, Fed. Rep. of Germany

[21] Appl. No.: 405,070

[22] Filed: Aug. 4, 1982

[30] Foreign Application Priority Data

Aug. 31, 1981 [DE] Fed. Rep. of Germany ....... 3134347

[51] Int. Cl.$^4$ ...................... B01J 31/40; C07C 51/56; C07C 51/54; C07C 67/37
[52] U.S. Cl. ...................... 502/33; 260/546; 260/549; 560/232; 562/517; 562/607
[58] Field of Search ............... 252/414; 260/549, 546; 562/607, 517; 423/22; 560/232; 502/24, 33, 31

[56] References Cited

U.S. PATENT DOCUMENTS 4,013,583  3/1977  Knifton ................... 252/415
4,252,983  2/1981  Erpenbach et al. ........ 260/546
4,333,884  6/1982  Kubbeler et al. .......... 260/549
4,476,237 10/1984  Porcelli .................. 502/31
4,476,238 10/1984  Palmer et al. ............ 502/31

FOREIGN PATENT DOCUMENTS 2054394  2/1981  United Kingdom ........... 252/411 R

Primary Examiner—P. E. Konopka
Attorney, Agent, or Firm—Connolly and Hutz

[57] ABSTRACT

The disclosure relates to a process for purifying and recovering a contaminated catalyst solution which is obtained in the carbonylation of methyl acetate and/or dimethylether, the catalyst solution containing carbonyl complexes of noble metals of group VIII of the Periodic System of the elements, quaternary heterocyclic aromatic nitrogen compounds or quaternary organophosphorus compounds as organic promoters, and optionally compounds of carbonyl-yielding common metals as inorganic promoters, undistillable organic contaminants as well as acetic acid, acetic anhydride and ethylidene diacetate. To this end, the disclosure provides for the catalyst solution to be distillatively freed from its volatile constituents and for the remaining solid distillation residue to be freed from the organic contaminants by extraction with aliphatic ethers; and for the remaining undissolved mixture of noble metal/carbonyl-complex, organic and optionally inorganic promoters to be filtered off and recycled into the carbonylation reaction.

6 Claims, No Drawings

PROCESS FOR PURIFYING AND RECOVERING CONTAMINATED CATALYST SOLUTION OBTAINED IN THE CARBONYLATION OF METHYL ACETATE AND/OR DIMETHYLETHER

The present invention relates to a process for purifying and recovering a contaminated catalyst solution which is obtained in the carbonylation of methyl acetate and/or dimethylether, the catalyst solution containing carbonyl complexes of noble metals of group VIII of the Periodic System of the elements, quaternary heterocyclic aromatic nitrogen compounds or quaternary organophosphorus compounds as organic promoters, and optionally compounds of carbonyl-yielding common metals as inorganic promoters, undistillable organic contaminants as well as acetic acid, acetic anhydride and ethylidene diacetate.

The recovery of rhodium or rhodium carbonyl complexes from catalyst systems contaminated with residues or from distillation residues has already been described, basically in connection with hydroformylation processes. The process described in DE-PS No. 12 90 535, for example, provides for rhodium-containing hydroformylation residue to be treated with an aqueous organic acid at elevated temperature, the rhodium complex becoming dissolved and being separated from the organic phase; rhodium is recovered in a yield of 82 up to 94%.

The process described in DE-AS No. 12 95 537 provides for the rhodium-containing reaction residue to be treated with steam under a pressure of 2 to 31 bars at 100° to 250° C. The catalyst becomes decomposed and rhodium sludge, which as such cannot be used again in the carbonylation reaction, is recovered by filtration under pressure.

Further processes for recovering rhodium or regenerating catalyst have been described in DE-OS No. 24 08 005 and DE-OS No. 26 14 799. As disclosed therein, the contaminated distillation residues originating from hydroformylation reactions are subjected initially to treatment with oxygen-containing mineral acids and peroxides, the treatment being intended to destroy rhodium and iridium carbonyl complexes and degrade the residues. After decomposition of peroxides in excess, the aqueous metal salt solutions are worked up by different methods. One of such method described in DE-OS No. 24 48 005 provides for the aqueous rhodium or iridium salt solution to be admixed at 0° up to 150° C. under pressure of 1 up to 250 bars with a water-soluble organic solvent, a hydrohalic acid or an alkali metal halide and a tertiary phosphine, and for the metals to be precipitated from the solution in the form of rhodium or iridium-carbonyl complexes with the use of carbon monoxide and additionally under hydrating conditions. As disclosed in DE-OS No. 26 14 799, rhodium +++ is first absorbed from the aqueous solution on a cation exchanger and then desorbed by means of hydrochloric acid. The hydrochloric acid solution is admixed with tertiary phosphines, treated with CO and, if desired, hydrogen, and rhodium is precipitated as a carbonyl complex.

The processes described, for example, in DE-OS No. 24 50 965; 28 36 084; 29 39 839 or 29 41 232 are, however, not of assistance in the purification and recovery of noble metal/carbonyl-complexes (Rh, Ir, Pd, Ru) and their promoters from the contaminated catalyst solutions obtained in the carbonylation of methyl acetate or dimethylether. The catalyst solution obtained in the carbonylation reaction is composed of 0.1 up to 10 weight % noble metal carbonyl complex, 40–70 weight % organic promoter, 1–10 weight % undistillable organic contaminants, and 20–40 weight % acetic acid, acetic anhydride and ethylidene diacetate. As can be inferred from the composition just indicated, it is possible for the catalyst solution to contain up to 80 weight % undistillable substances. After removal of volatile constituents by distillation, it would naturally be possible to subject the noble metal carbonyl-complex to oxidative degradation but this would simultaneously entail the destruction of the entire quantity of organic promoters whereby the beneficial effect which is associated with catalyst work up would be jeopardized from the onset.

Subjecting the residue to treatment with aqueous organic acids also entails adverse effects as the noble metal carbonyl-complex undergoes dissolution as well as the bulk of undistillable organic contaminants, which then cannot be separated from catalyst and promoter.

On subjecting the catalyst to decomposition with steam at elevated temperature, noble metal in elementary form, whose reconversion to the active catalyst complex is very expensive is obtained. In addition to this, water-insoluble organic residue which cannot readily be separated from the elementary noble metal is obtained.

The present invention which enables the adverse effects described hereinabove to be avoided now provides a process wherein distillative and extractive operation permit catalyst solution which is used in the carbonylation of methyl acetate and/or dimethylether and becomes gradually contaminated to be worked up in such a manner that it is possible for the noble metal/carbonyl-complex as well as for its promoters to be used again in the catalyst cycle, undistillable organic contaminants being removed therefrom. The present process compares favorably with the work-up methods described heretofore inasmuch as the extractants used for effecting work-up are cycled so that waste material is substantially not liable to pollute the environment. Only those undistillable organic contaminants which are formed during the process and reaction are removed for disposal by incineration, for example, in accordance with the pertinent art.

The present process comprises more particularly: distillatively freeing the catalyst solution from its volatile constituents; freeing the remaining solid distillation residue from the organic contaminants by extraction with aliphatic ethers; and filtering off the remaining undissolved mixture of noble metal/carbonyl-complex, organic promoters and optionally inorganic promoters, drying and recycling it into the carbonylation reaction.

Further preferred features of the present invention provide:

(a) for the distillation residue to be ether-treated at 30° to 90° C.;

(b) for 50 to 200 parts by weight ether to be used per part by weight distillation residue;

(c) for the solid distillation residue to be extracted with diethyl- or diisopropylether.

With respect to the origin of the contaminated catalyst solution, it is interesting to state that the reaction mixture cominig from the carbonylation reactor is separated distillatively into desirable final products, especially acetic anhydride, acetic acid and/or ethylidene diacetate, and unreacted cycled feed material on the one hand, and into catalyst solution as base material on the other hand. A portion of this catalyst solution which becomes gradually contaminated is taken from the catalyst solution cycle and distillatively freed in accordance with this invention, preferably at 100°–120° C. and 1–100 millibars from volatile matter, e.g. acetic acid, acetic anhydride and ethylidene diacetate.

The noble metals customarily contained in the contaminated catalyst solutions comprise rhodium, iridium, palladium and/or ruthenium which are present as carbonyl complexes e.g. of the formula $[CH_3P(C_4H_9)_3]_2Rh(CO)I_5$ or $CH_3P(C_4H_9)_3Rh(CO)_2I_2$. As organic promoters, the catalyst solutions generally contain one or more of the following heterocyclic aromatic nitrogen compounds or organophosphorus compounds.

(1) N-methylpyridinium iodide; N,N-dimethylimidazolium iodide; N-methyl-3-picolinium iodide; N-methyl-2,4-lutidinium iodide; N-methyl-3,4-lutidinium iodide, N-methyl-quinolinium iodide;

(2) tri-n-butyl-methyl-phosphonium iodide; trioctylmethyl-phosphonium iodide; trilauryl-methyl-phosphonium iodide; triphenyl-methyl-phosphonium iodide.

The catalyst solution may finally contain, as inorganic promoters, compounds of carbonyl-yielding common metals selected from Ce, Ti, Zr, Hf, Ge, Sn, Pb, V, Nb, Ta, As, Sb, Bi, Cr, Mo, W, Mn, Re, Fe, Co, Ni.

Next, the distillation residue which remains behind is extracted by means of an ether. In this way, the distillation residue is freed in a one-step operation from undistillable organic contaminants formed during the reaction; whilst the noble metal/carbonyl complex with the promoter(s) contained therein remains behind as undissolved residue. After removal of adhering ether, it is possible for the noble metal/carbonyl-complex and promoters to be recycled into the carbonylation reaction. Undistillable organic contaminants which are dissolved in the ether phase are incinerated after the ether has been expelled, which is used again for extraction. Needless to say, the process of this invention can be carried out continuously or discontinuously.

EXAMPLE 1

250 g catalyst solution cycled for methyl acetate carbonylation was taken from the catalyst cycle consisting of rhodium carbonyl complex ($L_2Rh(CO)I_5$; L=ligand), tri-n-butylmethylphosphonium iodide as an organic promoter, acetic anhydride, acetic acid, ethylidene diacetate, and organic contaminants and freed from distillable materials under reduced pressure of about 2 millibars and at a base temperature of up to 120° C. 81.5 g (32.6 weight %) distillate (25.8 weight % acetic acid, 73.8 weight % acetic anhydride and 0.4 weight % ethylidene diacetate) and 168.5 g distillation residue containing 0.433 g rhodium and 145.71 g tri-n-butylmethylphosphonium iodide (=2 weight % Rh-carbonyl complex and 58.3 weight % TBMPI, based on 250 g catalyst solution) were obtained. The distillation residue was placed in a mortar, comminuted therein and introduced into a Soxhlet-apparatus and freed therein from undistillable organic contaminants by extraction with 500 ml diisopropylether at the boiling temperature of the ether. After extraction over a period of 3 to 5 hours and drying, the ether was found to contain 152 g insoluble residue containing 0.430 g rhodium. In other words, the ether-insoluble residue was found to contain practically all of the rhodium carbonyl complex and the organic promoter used in the purification process. It was possible for it to be used again as such in the reaction. The diisopropylether phase was evaporated, and 16 g undistillable organic contaminants (=6.4 weight %, based on 250 g catalyst solution) which contained 0.012 weight % rhodium but was free from organic promoter were retained in the flask; this corresponded to a 99.5% rhodium yield in the purification process. The ether which had distilled off was used again for purification.

EXAMPLE 2

250 g catalyst solution cycled for dimethylether carbonylation was taken from the catalyst cycle consisting of acetic anhydride, acetic acid, ethylidene diacetate, rhodium carbonyl complex ($LRh(CO)_2I_2$; L=ligand), tri-n-butylmethylphosphonium iodide and undistillable organic contaminants, and freed from distillable matter under reduced pressure of 2 millibars at a base temperature of 120° C. 72 g (28.8 weight %) distillate (31 weight % acetic acid, 68.6 weight % acetic anhydride and 0.4 weight % ethylidene diacetate) and 178 g distillation residue containing 1.718 g rhodium and 156.3 g tri-n-butylmethylphosphonium iodide (=4.35 weight % Rh-carbonyl complex and 62.5 weight % TBMPI, based on 250 g catalyst solution) were obtained. The distillation residue was ground and introduced into a Soxhlet-apparatus and freed from undistillable organic contaminants by extraction with 500 ml diethylether at the boiling point of the ether. After extraction over a period of 3 to 5 hours and drying, 167.5 g ether-insoluble residue was obtained. It contained 1.70 g rhodium, corresponding to a yield of 99.0%. The ether-insoluble residue contained practically all of the rhodium carbonyl complex and organic promoter used in the purification. It was recycled to the reaction.

The diethylether phase was evaporated and 10.29 g undistillable organic contaminants (=4.12 weight %, based on 250 g catalyst solution) were retained in the flask. Analysis indicated that the residue still contained 0.09 weight % rhodium. The diethylether distilled off could be used again.

EXAMPLE 3

250 g catalyst solution cycled for methyl acetate carbonylation was taken from the catalyst cycle consisting of rhodium carbonyl complex ($L_2Rh(CO)I_5$; L=ligand), N,N-dimethylimidazolium iodide, undistillable organic contaminants, acetic acid, acetic anhydride and ethylidene diacetate, and freed from distillable matter under a reduced pressure of 2 millibars and a base temperature of up to 120° C., 64 g (25.6 weight %) distillate (29.3 weight % acetic acid, 70.3 weight % acetic anhydride and 0.4 weight % ethylidene diacetate) and 186 g distillation residue which contained 0.525 g rhodium and 161 g N,N-dimethylimidazolium iodide (=1.96 weight % Rh-carbonyl complex and 64.4 weight % DMII, based on 250 g catalyst solution) were obtained. The distillation residue was comminuted and introduced into a Soxhlet-apparatus and freed from undistillable organic contaminants by extraction with 500 ml diethylether at the boiling point of the ether. After extraction over a period of 3 to 5 hours and drying, 167 g ether-insoluble residue was obtained. It contained 0.520 g rhodium, corresponding to a yield of 99%. The ether-insoluble residue contained practically all of the rhodium carbonyl complex and organic promoter used in the purification. It was recycled into the reaction.

The diethylether phase was evaporated and 19 g undistillable organic contaminants (=7.6 weight %, based on 250 g catalyst solution) were retained in the flask. Analysis indicated that the residue still contained 0.026 weight % rhodium. The ether phase distilled off was used again for extraction.

EXAMPLE 4

250 g catalyst solution cycled for methyl acetate carbonylation was taken from the catalyst cycle consisting of palladium carbonyl complex, tri-n-butylmethylphosphonium iodide as organic promoter, undistillable organic contaminants, acetic acid, acetic anhydride and ethylidene diacetate, and freed from distillable matter at a base temperature of up to 120° C. and under a reduced pressure of 2 millibars. 80 g (32 weight %) distillate (51.9 weight % acetic acid, 10 weight % acetic anhydride and 38.1 weight % ethylidene diacetate) and 170 g distillation residue containing 0.85 g palladium and 152 g tri-n-butylmethylphosphonium iodide (=2 weight % Pd-carbonyl complex and 60.8 weight % TBMPI, based on 250 g catalyst solution) were obtained. The distillation residue was comminuted and introduced into a Soxhlet-apparatus and freed from undistillable organic contaminants by extraction with 500 ml diisopropylether at the boiling temperature of the ether. After extraction over 4 hours and drying, 159 g ether-insoluble residue was obtained. It contained 0.84 g palladium, corresponding to a yield of 98.8%. The ether-insoluble residue contained practically all of the palladium carbonyl complex and organic promoter used in the purification and was used again in the reaction.

The diisopropylether phase was evaporated and 11 g undistillable organic contaminants (=4.4 weight %, based on 250 g catalyst solution) which contained 0.03 weight % Pd were retained in the flask. The ether distilled off was used again for extraction.

We claim:

1. A process for purifying and recovering constituents from a contaminated catalyst solution which is obtained as a result of the carbonylation of methyl acetate, dimethylether or mixtures of methylacetate and dimethylether, the contaminated catalyst solution containing carbonyl compounds of noble metals of group VIII of the Periodic System of the elements, quaternary heterocyclic aromatic nitrogen compounds or quaternary organophosphorus compounds as organic promoters, undistillable organic contaminants, and volatile constituents including acetic acid, acetic anhydride and ethylidene diacetate, which comprises: distillatively freeing the catalyst solution from the volatile constituents; freeing the remaining solid distillation residue from the organic contaminants by extraction with an aliphatic ether; and filtering off the remaining undissolved mixture comprising noble metal/carbonyl-compound, and at least one of said organic promoters, and drying and recycling said remaining undissolved mixture into the carbonylation reaction.

2. A process as claimed in claim 1, wherein the distillation residue is ether treated at 30° to 90° C.

3. A process as claimed in claim 1, wherein 50 to 200 parts by weight ether are used per part by weight distillation residue.

4. A process as claimed in claim 1, wherein the solid distillation residue is extracted with diethyl- or diisopropylether.

5. A process as claimed in claim 1, wherein said contaminated catalyst solution further contains carbonyl compounds of non-noble metals.

6. A process as claimed in claim 5, wherein the carbonyl compounds of non-noble metals are filtered off with said remaining undissolved mixture and recycled into the carbonylation reaction.

* * * * *